US00PP20110P3

(12) United States Plant Patent
Sheehan

(10) Patent No.: US PP20,110 P3
(45) Date of Patent: Jun. 23, 2009

(54) GRAPEVINE 'SHEEGENE-13'

(50) Latin Name: *Vitis vinifera*
Varietal Denomination: Sheegene-13

(76) Inventor: Timothy P. Sheehan, 120 Olivewood Ct., Porterville, CA (US) 93257

( * ) Notice: Subject to any disclaimer, the term of this patent is extended or adjusted under 35 U.S.C. 154(b) by 0 days.

(21) Appl. No.: 11/897,629

(22) Filed: Aug. 30, 2007

(65) Prior Publication Data

US 2009/0064379 P1 Mar. 5, 2009

(51) Int. Cl.
*A01H 5/00* (2006.01)

(52) U.S. Cl. ..... Plt./205

(58) Field of Classification Search ..... Plt./205
See application file for complete search history.

*Primary Examiner*—June Hwu
(74) *Attorney, Agent, or Firm*—Baker Manock & Jensen; Eric C. Cole

(57) ABSTRACT

A new and distinct variety characterized by the large, red-colored seedless grapes that ripen in late August to early September, approximately six weeks later than the Flame Seedless Grape (unpatented) when grown in the San Joaquin Valley of Central California. The grapes of this new variety are produced on strong woody stems and branches and are well adapted to commercial harvesting.

1 Drawing Sheet

Latin name of the genus and species of the plant claimed:

The claimed plant relates to a new and distinct variety of *Vitis vinifera* to be known as 'Sheegene-13'.

Variety denomination:

This invention relates to a new discovery and asexual reproduction of a new variety of *Vitis vinifera*. The new variety was first hybridized by Timothy P. Sheehan of Porterville Calif. in Spring 2000; first flowering occurred in May 2003. The pollen parent is Princess (unpatented) and the seed parent is Red Globe (U.S. Plant Pat. No. 4,787). The new variety was asexually propagated in the dormant season of 2003/2004, bud grafted on Harmony, virus free rootstock near Fowler, Calif. Five vines were planted at that time in a *Vitis vinifera* variety block located near Fowler, Calif. on the west side of Thompson Road, north of Adams Road. The red-colored seedless grapes produced by the new variety are large in size and mature approximately six weeks later than Flame Seedless (unpatented). The new variety has been shown to maintain its distinguishing characteristics through asexual propagation.

The new variety is distinguished from its pollen parent, Princess (unpatented), in that the new variety produces red-colored seedless grapes, as compared to the white-colored seedless grapes produced by its pollen parent, Princess (unpatented). The new variety is distinguished from its seed parent, Red Globe (U.S. Plant Pat. No. 4,787), in that the new variety produces seedless grapes, as compared to its seed parent, Red Globe (U.S. Plant Pat. No. 4,787), that produces seeded grapes.

BACKGROUND OF THE INVENTION

The present invention relates to a new and distinct variety of grape which will hereinafter be denominated as 'Sheegene-13' and more particularly as a grapevine that produces a red-colored large seedless grape that matures approximately from the fourth week of August to the first week of September in the San Joaquin Valley of Central California. The new invention closely resembles Flame Seedless (unpatented) but it produces a large sized grape with excellent flavor and matures approximately six weeks later.

SUMMARY OF THE INVENTION

The 'Sheegene-13' grapevine is characterized by producing a large, red-colored seedless grape that is mature for harvesting and shipment approximately from the fourth week in August to the first week in September in the San Joaquin Valley of Central California. The new variety can be compared to Flame Seedless (unpatented) but the grapes mature approximately six weeks later, among other distinguishing characteristics.

BRIEF DESCRIPTION OF THE DRAWINGS

The accompanying drawing is a colored photograph of the grapes produced by the subject variety; several leaves are displayed as well as a typical section of the vine. Across the top of the color photograph to the left displays a shoot and tendrils and small leaves; and to the right is a large leaf displaying the bottom side, attached to a petiole. Below the shoot and tendrils and small leaves is a secondary growth cluster. Across the middle of the color photograph on the left is a mature grape cluster; and to the right is a mature leaf displaying the upper surface, attached to the petiole. Below the mature leaf is a secondary growth cluster. Across the bottom of the color photograph to the left is a small shoot with tendrils; in the center are four grapes cut in half longitudinally as well as horizontally displaying the flesh and shape; and to the right is a mature cane displaying tendrils, nodes, and small leaves.

DETAILED BOTANICAL DESCRIPTION

Referring more to the horticultural description of the new and distinct variety of grapevine, the following has been observed under the ecological conditions prevailing at the origin vineyard located near Fowler, Calif. in the San Joaquin Valley of Central California. All major color designations are by reference to the Dictionary of Color by Maerz and Paul, First Edition, published in 1930. Common color names are also used in several instances.

Vine:

*Size.*—5 feet (1.52 meters) in height; 30 to 36 inches (76.20 to 91.44 cm) in width.
*Vigor.*—Very good.
*Figure.*—Wide cordons forming a "T" shaped figure.
*Production Capacity.*—Very good.
*Regularity of bearing.*—Regular.

Trunk:

*Size.*—Medium; 6 inches (15.24 cm) in circumference, 28 inches (71.12 cm) above graft.
*Surface texture.*—Rough, shaggy.
*Mature cane color.*—P1.14 L12 Sudan Brown.
*Nodes.*—Four nodes on canes, 12⅓ inches (31.33 cm) in length.
*Length between nodes.*—5 inches (12.7 cm).
*Lenticel number.*—30.
*Lenticel size.*—0.
*Shoot size.*—Medium.
*Shoot length.*—2.24 inches (58 mm).
*Shoot shape.*—Droopy.
*Tendril number.*—1.
*Tendril length.*—2.24 inches (58 mm).
*Tendril location.*—At nodes.
*Tendril form.*—Bifurcate.
*Tendril texture.*—Firm.
*Bud shape.*—Convex.
*Bud size.*—0.24 inches (6 mm) in length; 0.31 inches (8 mm) in width.
*Bud fruitfulness.*—Very good.
*Bud break date.*—N/A.

Branches:

*Size.*—Medium; 2 inches (5.04 cm) in circumference.
*Cordons.*—36 inches (91.4 cm) from trunk on one each.
*Color* (*One year older wood*).—P1.7 H11 Casserole Rustic Brown.
*Color* (*Immature branches*).—P1.20 H6 — Piquant Green.

Leaves:

*Size.*—Large.
*Density.*—Dense.
*Average length.*—6.3 inches (16.0 cm).
*Average width.*—7.87 inches (20.0 cm).
*Shape.*—Pentagonal.
*Texture* (*upper surface*).—Smooth.
*Texture* (*lower surface*).—Glabrous.
*Color* (*upward disposed surface*).—P1.23 J8 Mt. Vernon Green.
*Color* (*downward disposed surface*).—P1.20 K7 Piquant Green.
*Color* (*leaf vein*).—P1.20 K6 Piquant Green.
*Glandular characteristics.*—0.
*Petiole size.*—Large.
*Petiole color.*—P1.20 K7 Piquant Green.
*Petiole length.*—5.71 to 6.54 inches (14.5 to 16.6 cm).
*Petiole thickness.*—0.12 to 0.138 inches (3 to 3.5 mm).
*Petiole sinus form.*—Upside down "U" shape.
*Lobe* (*average*).—Four.
*Tooth size.*—Variable; 0.43 to 0.55 inches (11 to 14 mm) in length, 0.51 to 0.59 inches (13 to 15 mm) in width.
*Tooth number.*—Four between lobes.
*Tooth shape.*—Convex.

Inflorescence:

*Size.*—Cluster is 6½ to 7 inches (16.4 to 17.78 cm) in length.
*Number borne per spur.*—2.
*Number borne per vine.*—20 to 24.

Flowers:

*Flower bud size.*—Small.
*Flower bud surface.*—Glabrous.
*Flower bud quantity.*—Moderate.
*Date of bloom.*—Apr. 29, 2007.
*Date of full bloom.*—May 7, 2007
*Size of bloom.*—12 inches (3 mm).
*Petal color.*—P1.19 k10 Bud gr.
*Petal size.*—0.079 inches (2 mm).
*Pistil color.*—P1.17 L7 viridine y.
*Date of first visible berries.*—May 7, 2007.
*Berry size.*—Generally small; approximately 0.079 inches (2 mm).

Fruit:

*Solids.*—19.5° Brix.
*Acids.*—0.40.
*Sugar/Acid ratio.*—4.87.
*Juice ph.*—3.84.
*Seeds.*—Rudimentary.
*Seed number.*—2.
*Cap stem pedicel.*—0.31 inches (8 mm).
*Berry weight.*—11.36 grams.
*Juice color.*—P1.1 B7 Pink+.
*Size.*—Large.
*Cluster size.*—Large.
*Cluster weight.*—1704 grams (3¾ lbs.).
*Cluster average length* (*Not including main stem of cluster*).—8.46 inches (22.0 cm).
*Cluster average width* (*at greatest width*).—7.087 inches (18.0 cm).
*Cluster form.*—Conical.
*Compact.*—Compact.
*Stem.*—Generally medium; 1.57 inches (4 cm).
*Stem caliper.*—0.20 inches (5 mm).
*Berry size* (*average dimension along longitudinal axis*) .—1.10 (28 mm).
*Berry size* (*average dimension along transverse axis*) .—3 0.91 inches (23 mm).
*Berry shape.*—Ovate.
*Berry number.*—88.

Flesh:

*Flesh color.*—P1.6 A2 close to Rosebud.
*Juice production.*—Very good.
*Flavor.*—Very good.
*Aroma.*—Very mild.
*Texture.*—Firm.
*Ripening.*—Even.
*Eating quality.*—Very good.

Skin:

*Skin thickness.*—Thin.
*Texture.*—Tough.
*Blush color.*—P1.55 J12 Dahlia P1.
*Ground color.*—P1.55 C4 close to Wineberry.
*Pulp.*—Clear.
*Lenticel.*—None.
*Use.*—Fresh market

*Keeping quality.*—Very good.

*Resistance to disease.*—None observed.

*Harvesting and shipment.*—Late August to early September in the San Joaquin Valley of Central California.

*Shipping and handling quality.*—Very good.

*U.S.D.A hardiness zone.*—Zones 8 and 9.

Having thus described and illustrated our new variety of grapevine, we claim:

1. A new variety of grapevine to be known as 'Sheegene-13', substantially as illustrated and described, characterized principally by its production of large, red-colored seedless grapes, that mature approximately six weeks later in the season of ripening that does the Flame Seedless Grape (unpatented) that it closely resembles.

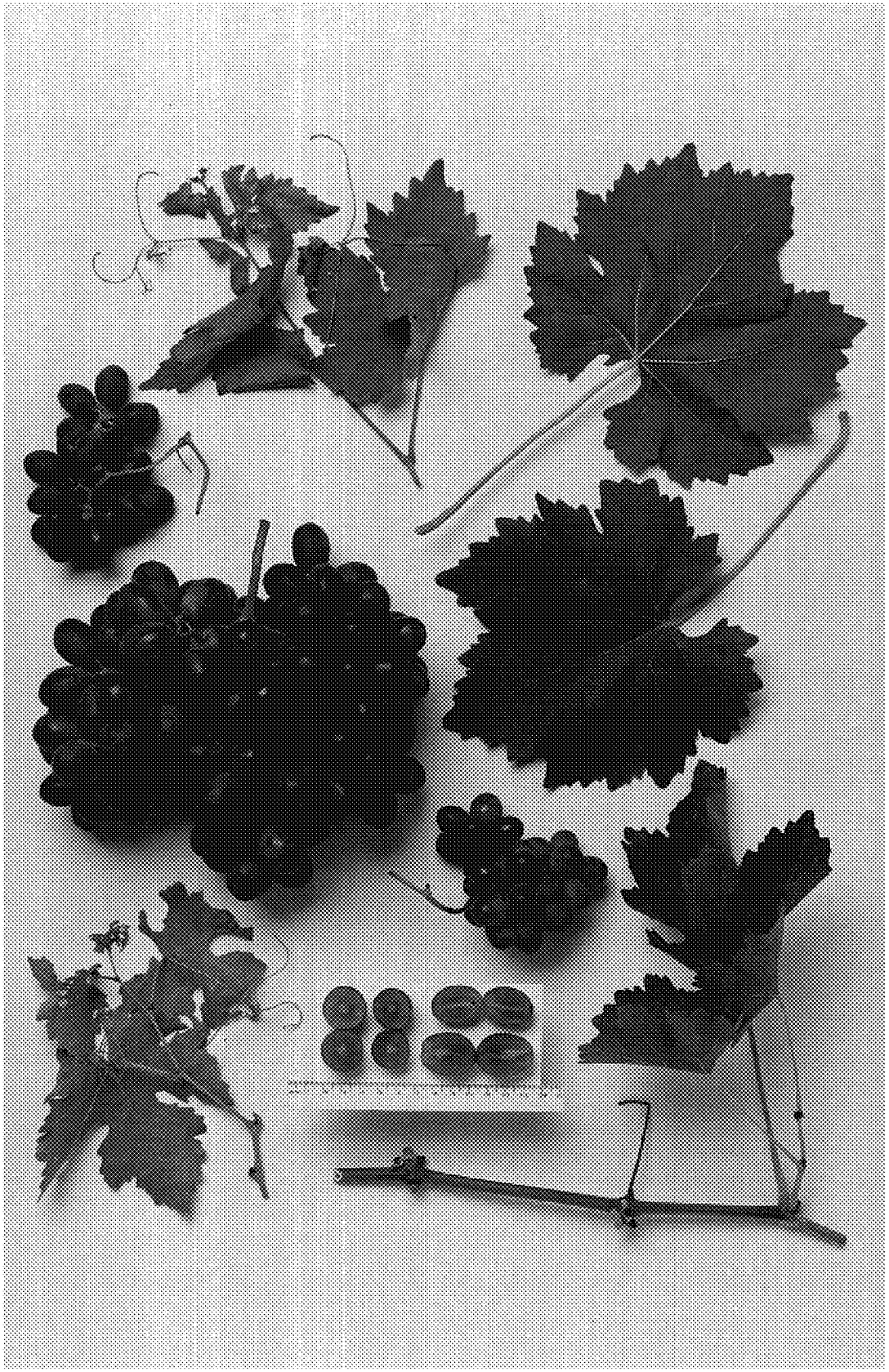

* * * * *